United States Patent
Park et al.

(10) Patent No.: US 12,274,886 B2
(45) Date of Patent: Apr. 15, 2025

(54) MULTI LEADLESS PACEMAKER AND SURGICAL DEVICE

(71) Applicants: INDUSTRY FOUNDATION OF CHONNAM NATIONAL UNIVERSITY, Gwangju (KR); KOREA INSTITUTE OF MEDICAL MICROROBOTICS, Gwangju (KR)

(72) Inventors: Jong-Oh Park, Gyeonggi-do (KR); Chang-Sei Kim, Gwangju (KR); Ayoung Hong, Daegu (KR); Ja Young Kim, Daejeon (KR); Seong Hwan Jeong, Gwangju (KR)

(73) Assignees: INDUSTRY FOUNDATION OF CHONNAM NATIONAL UNIVERSITY, Gwangju (KR); KOREA INSTITUTE OF MEDICAL MICROROBOTICS, Gwangju (KR)

( * ) Notice: Subject to any disclaimer, the term of this patent is extended or adjusted under 35 U.S.C. 154(b) by 653 days.

(21) Appl. No.: 17/283,817

(22) PCT Filed: Nov. 3, 2020

(86) PCT No.: PCT/KR2020/015198
§ 371 (c)(1),
(2) Date: Apr. 8, 2021

(87) PCT Pub. No.: WO2022/059840
PCT Pub. Date: Mar. 24, 2022

(65) Prior Publication Data
US 2022/0305274 A1 Sep. 29, 2022

(30) Foreign Application Priority Data
Sep. 16, 2020 (KR) .................. 10-2020-0119255

(51) Int. Cl.
*A61N 1/375* (2006.01)
*A61N 1/365* (2006.01)
*A61N 1/372* (2006.01)

(52) U.S. Cl.
CPC ..... *A61N 1/37512* (2017.08); *A61N 1/36507* (2013.01); *A61N 1/37288* (2013.01); *A61N 1/3756* (2013.01)

(58) Field of Classification Search
CPC .............. A61N 1/3765; A61N 1/37288; A61N 1/36507; A61N 1/37512
See application file for complete search history.

(56) References Cited

U.S. PATENT DOCUMENTS

6,505,082 B1   1/2003   Scheiner et al.
11,154,706 B1*  10/2021  Fishel .................. A61B 5/29
(Continued)

*Primary Examiner* — Rex R Holmes
*Assistant Examiner* — Jennifer L Ghand
(74) *Attorney, Agent, or Firm* — Harness, Dickey & Pierce, P.L.C.

(57) ABSTRACT

The disclosed pacemaker module includes a case unit, a vertical movement guide, an atrial sensor, and a pacemaker. The pacemaker module according to the present disclosure has an excellent effect in that it is capable of accurately measuring the flow of current in the entire heart and capable of being accurately and consistently operated with a simple operation, which makes it possible to accurately implant the pacemaker module.

7 Claims, 11 Drawing Sheets

(56) References Cited

U.S. PATENT DOCUMENTS

| | | | |
|---|---|---|---|
| 2004/0006301 A1* | 1/2004 | Sell | A61M 25/0127 606/39 |
| 2006/0052656 A1* | 3/2006 | Maghribi | A61N 1/0541 600/12 |
| 2006/0142829 A1* | 6/2006 | Maschke | A61N 1/0568 607/120 |
| 2009/0018599 A1* | 1/2009 | Hastings | A61N 1/372 607/32 |
| 2010/0125311 A1* | 5/2010 | Choi | A61N 1/0541 607/45 |
| 2014/0172034 A1* | 6/2014 | Bornzin | A61N 1/368 607/9 |
| 2015/0088155 A1* | 3/2015 | Stahmann | A61N 1/0587 606/129 |
| 2016/0067490 A1* | 3/2016 | Carney | A61N 1/37276 607/17 |
| 2016/0310723 A1* | 10/2016 | Eggen | A61N 1/3756 |
| 2016/0310726 A1* | 10/2016 | Demmer | A61N 1/3756 |
| 2018/0021581 A1 | 1/2018 | An et al. | |
| 2018/0028805 A1* | 2/2018 | Anderson | A61N 1/37205 |
| 2019/0038906 A1* | 2/2019 | Koop | A61N 1/37205 |
| 2021/0069517 A1* | 3/2021 | Foster | A61N 1/37518 |

* cited by examiner

MULTI LEADLESS PACEMAKER AND SURGICAL DEVICE

CROSS-REFERENCE TO RELATED APPLICATIONS

This application is a national phase entry of PCT Application No. PCT/KR2020/015198, filed on Nov. 3, 2020, which claims the benefit and priority of Korean Patent Application No. 10-2020-0119255, filed on Sep. 16, 2020. The entire disclosure of the above applications is incorporated herein by references.

TECHNICAL FIELD

The present disclosure was made by Task Unique No. 190642, Task No. HI19C0642 under the support of the Korean Ministry of Health and Welfare. The research management institution for the above project is the Korea Health Industry Development Institute, the research business name is "Micro Medical Robot Commercialization Technology Development", and the research project name is "Micro Medical Robot Commercialization Common Base Technology Development Center". The host institute is the Korean Micro Medical Robot Research Institute, and the research period is from Jun. 12, 2019 to Dec. 31, 2022.

The present disclosure relates to a multi leadless pacemaker and surgical device. More specifically, the present disclosure relates to a pacemaker module in which a case unit, a vertical movement guide, an atrial sensor, and a pacemaker are integrated. The pacemaker module according to the present disclosure is capable of preventing damage to the inside of a human body during implantation, and capable of controlling the heartbeat while measuring the microcurrent and current flow of a heart.

BACKGROUND ART

A pacemaker is a device that controls the heartbeat by applying electrical stimulation to the heart, and is mainly applied to a patient who complains of symptoms of bradyarrhythmia.

A conventional pacemaker includes a pacemaker body (a generator), a lead, and an electrode for transmitting stimulation pulses to a myocardium, and the pacemaker body and the electrode are connected to each other by the lead. The pacemaker body is placed under the skin of the left chest, and an electrode guide line is placed in the right atrium and the right ventricle through the left subclavian vein so as to control the heartbeat. However, the conventional pacemaker has the following problems.

In the conventional pacemaker, since the pacemaker body and the electrode are connected by the lead, a disconnection of the lead may occur. A pacing defect may occur due to the disconnection of the lead, and a pocket infection that infects human tissue may occur at the inserted location. In addition, there is a drawback in terms of beauty since the pacemaker is inserted under the skin. Moreover, a paging defect may occur due to the displacement of the electrode early after the implantation of the pacemaker, and when the displacement of electrode occurs, an excessive burden may be placed on the patient, which inevitably leads to reoperation.

In recent years, in order to solve these problems, a leadless pacemaker that does not use an electrode guide line has been developed. The leadless pacemaker is inserted through the inferior vena cava and is placed in a ventricle so as to control the heartbeat. Due to the removal of an electrode guide line, such a leadless pacemaker has an advantage over the conventional pacemaker in that there are no problems such as pocket infection, hematoma, a cosmetic disadvantage, and damage to an electrode guide line.

However, the leadless pacemaker also has problems. The conventional leadless pacemaker is located in a ventricle and is difficult to measure a conduction process of the entire heart in the ventricle. Thus, it is difficult to accurately measure the conduction process of the entire heart. In addition, there is a problem in that the outcome of implantation surgery varies depending on the skill of a doctor.

In this background, there is a need for a device capable of accurately measuring the conduction process of the entire heart and capable of accurately and consistently implanting a pacemaker with a simple implantation operation.

SUMMARY

Technical Problem

Thus, the inventors made a pacemaker module including a case unit, a vertical movement guide, an atrial sensor, and a pacemaker, and have found that there is an excellent effect in that the pacemaker module according to the present disclosure is capable of accurately measuring the flow of current in the entire heart and capable of being accurately and consistently operated with a simple operation, which makes it possible to accurately implant the pacemaker module.

Accordingly, the present disclosure provides a pacemaker module including a case, a vertical movement guide, an atrial sensor, and a pacemaker.

In another aspect, the present disclosure provides a use of a pacemaker module including a case, a vertical movement guide, an atrial sensor, and a pacemaker.

Technical Solution

The present disclosure relates to a multi leadless pacemaker and surgical device. The pacemaker module according to the present disclosure has advantages of being easy and simple to operate while being able to accurately measure the current flow in the heart.

Hereinafter, the present disclosure will be described in more detail.

An aspect of the present disclosure relates to a pacemaker module including: a case unit through which a vertical movement guide wire, a atrial sensor re-coupling wire, and a pacemaker re-coupling wire pass; a vertical movement guide connected to the vertical movement guide wire and including a hole port through which the atrial sensor re-coupling wire and the pacemaker re-coupling wire pass; an atrial sensor connected to the atrial sensor re-coupling wire and including a first sensor; and a pacemaker connected to the pacemaker re-coupling wire and including a stimulation unit and a second sensor.

In an embodiment of the present disclosure, the case unit may include, but is not limited to, any one or more materials selected from a group consisting of rubber, carbon composite, synthetic resin, polyurethane, silicone, polyethylene, pebax, and polypropylene.

In an embodiment of the present disclosure, the case unit may include a magnetic body.

The magnetic body may be made of a material selected from iron, nickel, cobalt, or an alloy thereof, or a permanent magnet without limitation as long as it exhibits magnetism, or the like. For example, the magnetic material may be, but is not limited to, a permanent magnet.

When the case unit includes a magnetic body, it is possible to freely and precisely drive the case unit within a human body using an external driving device. Specifically, the external driving device may include a permanent magnet or an electromagnet. By applying a magnetic field to the magnetic body of the case unit using the external driving device, it is possible for the user to freely move the pacemaker module within a human body only using the external driving device. Alternatively, it is possible for the user to move the pacemaker module to a desired location within a human body by operating the external driving device with a feeder connected to a wire tube communicating with the case unit.

In an embodiment of the present disclosure, the case unit may include an ejection port in one side thereof, and the vertical movement guide, the atrial sensor, and the pacemaker may move inside and outside the case unit through the ejection port.

In an embodiment of the present disclosure, the vertical movement guide, the atrial sensor, and the pacemaker may be arranged in the order of the vertical movement guide, the atrial sensor, and the pacemaker from the side opposite to the ejection port.

In an embodiment of the present disclosure, the case unit may have a rotational motion guide arranged on the inner surface thereof.

In an embodiment of the present disclosure, the rotational motion guide may include a recess, and the recess may have a spiral shape.

In an embodiment of the present disclosure, the pacemaker module may include a wire tube connected to one end of the case unit.

In an embodiment of the present disclosure, the wire tube may include, but is not limited to, one or more selected from a group consisting of rubber, a carbon composite, a synthetic resin, polyurethane, synthetic fiber, silicone, polyethylene, nylon, carbon fiber, and polypropylene.

The wire tube may include a hollow interior, and accordingly, the vertical movement guide wire, the atrial sensor re-coupling wire, and the pacemaker re-coupling wire may be arranged inside the wire tube, and the vertical movement guide wire, the atrial sensor re-coupling wire, and a pacemaker re-coupling wire are independently movable within the wire tube according to the user's manipulation.

In an embodiment of the present disclosure, the wire tube may include a tube including one or more one or more hollow interiors. For example, the wire tube may include a vertical movement guide wire tube through which the vertical movement guide wire moves, an atrial sensor re-coupling wire tube through which the atrial sensor re-coupling wire moves, and a pacemaker re-coupling wire tube through which the pacemaker re-coupling wire moves. When the three types of tubes described above are arranged in the wire tube, respective wires are movable inside the wire tubes without interference with each other.

In an embodiment of the present disclosure, the pacemaker module may further include a manipulation unit connected to one end of the wire tube.

In the present disclosure, it is possible for the user to manipulate the pacemaker module by manipulating the vertical movement guide wire, the atrial sensor re-coupling wire, and the pacemaker re-coupling wire through the manipulation unit.

In an embodiment of the present disclosure, the vertical movement guide wire may include a metal or synthetic fiber. For example, the vertical movement guide wire may include, but is not limited to, one or more materials selected from a group consisting of a shape memory alloy, carbon fiber, and nylon.

The vertical movement guide is connected to the vertical movement guide wire. Accordingly, it is possible for the user to eject the atrial sensor and the pacemaker from the inside of the case unit to the outside of the case unit by manipulating the vertical movement guide wire to push the vertical movement guide wire to the outside of the case unit.

In an embodiment of the present disclosure, the atrial sensor re-coupling wire may include a metal or synthetic fiber. For example, the vertical movement guide wire may include, but is not limited to, one or more materials selected from a group consisting of a shape memory alloy, carbon fiber, and nylon.

In an embodiment of the present disclosure, the pacemaker re-coupling wire may include a metal or synthetic fiber. For example, the vertical movement guide wire may include, but is not limited to, one or more materials selected from a group consisting of a shape memory alloy, carbon fiber, and nylon.

In the present disclosure, the atrial sensor may measure an electrical signal of an atrium through the first sensor.

The atrial sensor is mounted in the atrium, and is capable of detecting and recording the ECG information of the heart, converting the ECG information into a digital signal, and outputting the digital signal to the outside. The atrial sensor detects electrocardiogram information of a heart. The detected electrocardiogram information may detect, but is not limited to, for example, P waves, a QRS group, T waves or a Q-T time, an A-H time, an H-V time, etc.

In an embodiment of the present disclosure, the atrial sensor may include a transmission unit, and the transmission unit may transmit the ECG information of the heart measured by the atrial sensor to the pacemaker or a controller.

In an embodiment of the present disclosure, the atrial sensor may include a first battery unit.

The first battery unit may supply power for the operation of the atrial sensor and the first sensor, and the first battery unit may include a lithium ion battery, a fuel cell, or a biofuel cell.

In an embodiment of the present disclosure, the atrial sensor may include at least one first protrusion engageable with the rotational motion guide.

The first protrusion is arranged on a side surface portion of the atrial sensor to be engageable with the rotational motion guide, thereby stably coupling the atrial sensor inside the case unit.

In an embodiment of the present disclosure, the atrial sensor may include a first re-coupling loop.

The first re-coupling loop may be arranged on one side of the atrial sensor, and the atrial sensor re-coupling wire may be connected to the first re-coupling loop.

In the present disclosure, the pacemaker may output cardiac stimulation pulses that stimulate heart tissue through a stimulation unit, and may sense an electrical signal of a ventricle through the second sensor.

The stimulation unit may adjust stimulation intensity and intervals of stimulation pulses based on the atrial electrocardiogram information received from the atrial sensor and the electrical signal of the ventricle measured by the second sensor, and may output the cardiac stimulation pulses to the heart.

In an embodiment of the present disclosure, the pacemaker may include a reception unit configured to receive a signal from the controller or the atrial sensor.

In an embodiment of the present disclosure, the pacemaker may include a second battery unit.

The second battery unit may supply power for the operation of the pacemaker and the second sensor, and the second battery unit may include a lithium ion battery, a fuel cell, or a biofuel cell.

In an embodiment of the present disclosure, the stimulation unit may include an electrode.

In an embodiment of the present disclosure, an electrode from which cardiac stimulation pulses are output may be arranged on a surface of the second sensor.

In an embodiment of the present disclosure, the pacemaker may include at least one second protrusion engageable with the rotational motion guide.

The second protrusion may be arranged on a side surface portion of the pacemaker to be engageable with the rotational motion guide. Accordingly, the second protrusion may stably couple the pacemaker inside the case unit.

In an embodiment of the present disclosure, an electrode may be arranged on the surface of the second protrusion.

In an embodiment of the present disclosure, the pacemaker may include a second re-coupling loop.

The second re-coupling loop may be arranged on one side of the pacemaker, and the pacemaker re-coupling wire may be connected to the second re-coupling loop.

In an embodiment of the present disclosure, the pacemaker module may further include a controller.

The controller may receive ECG information output from the atrial sensor and may output a control signal of the pacemaker based on the ECG information such that the pacemaker may output cardiac stimulation pulses that electrically stimulate the heart tissue.

In an embodiment of the present disclosure, a first fixing part and a second fixing part may each have a linear shape, a curved shape, or a spiral shape. For example, the first fixing part and the second fixing part may have, but is not limited to, a spiral shape for stable coupling with the heart tissue.

In the present disclosure, the atrial sensor and the pacemaker may be connected to each other in a wireless or wired manner.

In an embodiment of the present disclosure, the atrial sensor and the pacemaker may be connected to each other via a data transmission wire.

Advantageous Effects

The present disclosure relates to a pacemaker module including a case unit, a vertical movement guide, an atrial sensor, and a pacemaker. The pacemaker module according to the present disclosure has an excellent effect in that it is capable of accurately measuring the flow of current in the entire heart and capable of being accurately and consistently operated with a simple operation, which makes it possible to accurately implant the pacemaker module.

MODE FOR CARRYING OUT THE INVENTION

A pacemaker module including: a case unit through which a vertical movement guide wire, a atrial sensor re-coupling wire, and a pacemaker re-coupling wire pass; a vertical movement guide connected to the vertical movement guide wire and including a hole port through which the atrial sensor re-coupling wire and the pacemaker re-coupling wire pass; an atrial sensor connected to the atrial sensor re-coupling wire and including a first sensor; and a pacemaker connected to the pacemaker re-coupling wire and including a stimulation unit and a second sensor.

DETAILED DESCRIPTION

Hereinafter, embodiments of the present disclosure will be described in detail with reference to the accompanying drawings. In the following description of the present disclosure, a detailed description of related known functions or configurations will be omitted when it is determined that the detailed description may make the subject matter of the present disclosure unnecessarily unclear.

Embodiments according to the concept of the present disclosure may be variously modified and may be implemented in various forms. Thus, specific embodiments are illustrated in the drawings, and will be described in detail in the present specification or application. However, it is to be understood that this is not intended to limit the embodiments according to the concept of the present disclosure to the specific disclosure forms, but all the modifications, equivalents, and substitutions fall within the spirit and scope of the present disclosure.

When a constituent element is referred to as being "connected" or "coupled" to another constituent element, it should be understood that the constituent element may be directly connected or coupled to the other element, but a still another constituent element may be present therebetween.

Whereas, when a constituent element is referred to as being "directly connected" or "directly coupled" to another element, it should be understood that there is no constituent element therebetween. Other expressions that describe a relationship between constituent elements, such as "between" and "just between" or "neighboring to" and "directly neighboring to" should be interpreted in the same manner as the foregoing.

Figure 1:
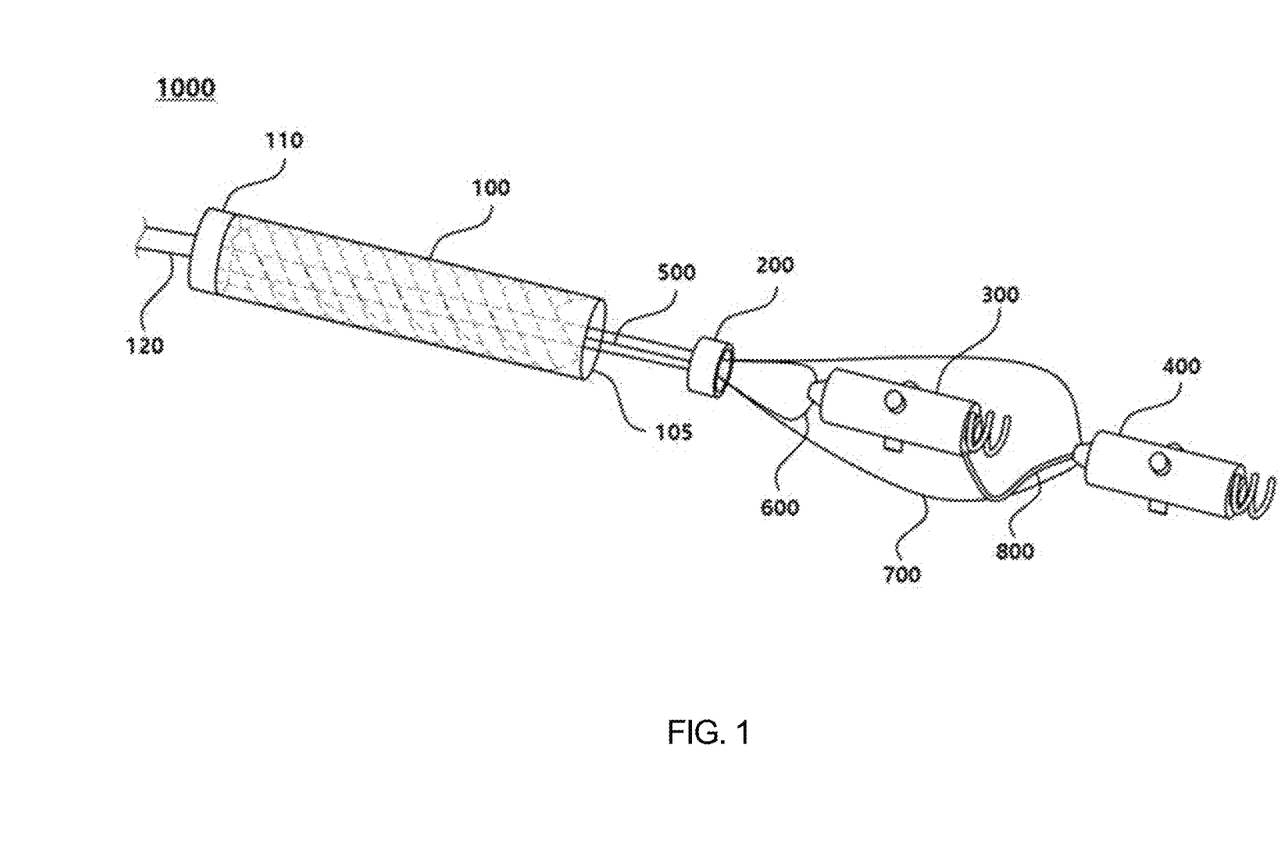
FIG. 1 is a view illustrating a pacemaker module according to an embodiment of the present disclosure.

FIG. 1 is a view illustrating a pacemaker module according to an embodiment of the present disclosure.

Referring to FIG. 1, a pacemaker module 1000 according to an embodiment may include a case unit 100, a vertical movement guide 200, an atrial sensor 300, a pacemaker 400, a vertical movement guide wire 500, an atrial sensor re-coupling wire 600, a pacemaker re-coupling wire 700, and may include a data transmission wire 800.

The case unit 100 may include a soft and flexible material. For example, the case unit 100 may include one or more materials selected from a group consisting of rubber, a carbon composite, a synthetic resin, polyurethane, silicone, polyethylene, pebax, and polypropylene. Since the case unit includes a soft and flexible material, it is possible to move the pacemaker module while minimizing damage to human tissue when moving the pacemaker module within the human body.

The case unit 100 may include an ejection port 105 in one side. The ejection port 105 may be located at a position opposite to the a magnetic body 110, and the vertical movement guide 200, the atrial sensor 300, and the pacemaker 400 are movable to the inside and outside through the ejection port 105 in the case unit 100.

The case unit 100 may include a magnetic body 110. The magnetic body may be, but is not limited to, iron, nickel, cobalt, or an alloy thereof, or a permanent magnet.

As illustrated in FIG. 1, when the case unit 100 includes the magnetic body 110, it is possible for a user to move the case unit 100 to a desired location in the human body by applying a magnetic field to the case unit 100 by manipulating an external driving device including a permanent magnet or an electromagnet.

The wire tube 120 may be connected to one end of the case unit 100.

The wire tube 120 may include one or more materials selected from a group consisting of rubber, a carbon composite, a synthetic resin, polyurethane, synthetic fiber, silicone, polyethylene, nylon, carbon fiber, and polypropylene.

The wire tube 120 may include a hollow interior. Inside the wire tube 120, a vertical movement guide wire 500, an atrial sensor re-coupling wire 600, and a pacemaker re-coupling wire 700 may be arranged.

A tube including one or more hollow interiors may be arranged inside the wire tube 120. For example, a vertical guide wire tube including a hollow interior, an atrial sensor re-coupling wire tube, and a pacemaker re-coupling wire tube may be arranged inside the wire tube. In this case, since the wires move in respective tubes independent from each other, it is possible to minimize interference between the wires.

A manipulation unit (not illustrated) may be arranged at the other end of the wire tube 120. That is, a manipulation unit may be arranged at one end of the wire tube 120 opposite to the case unit 100.

The user may move the vertical movement guide 200, the atrial sensor 300, and the pacemaker 400 by manipulating each of the vertical movement guide wire tube 500, the atrial sensor re-coupling wire tube 600, and the pacemaker re-coupling wire tube 700 of the pacemaker module using the manipulation unit.

The vertical movement guide wire 500 may be arranged to pass through the wire tube 120 and the case portion 100 and to be connected to the vertical movement guide 200.

The vertical movement guide wire 500 may include a metal or synthetic fiber, and may include, for example, one or more materials selected from a group consisting of a shape memory alloy, carbon fiber, or nylon.

The vertical movement guide 200 may include a hole port through which the atrial sensor re-coupling wire 600 and the pacemaker re-coupling wire 700 pass, and may be arranged to be connected to the vertical movement guide wire 500.

Therefore, it is possible for the user to move the vertical movement guide 200 toward the ejection port 105 in the case unit 100 by manipulating the manipulating unit, and as the vertical movement guide 200 moves toward the ejection port 105, to eject the atrial sensor 300 and the pacemaker 400 from the case unit 100.

Figure 4:
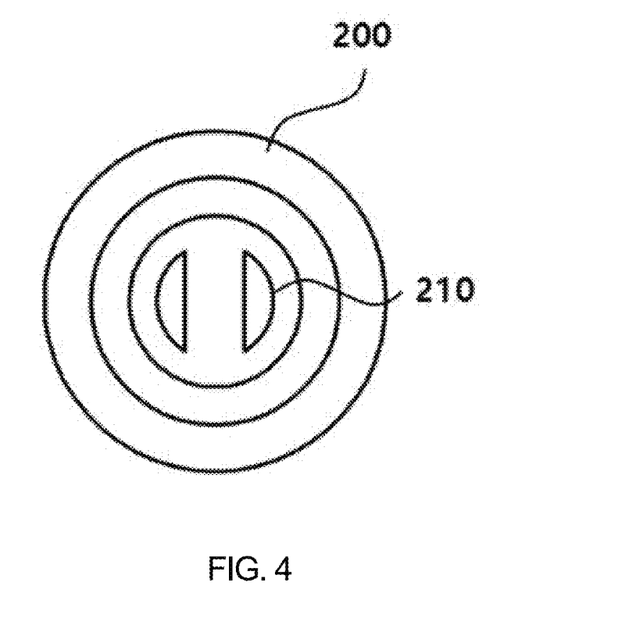
FIG. 4 is a front view of a vertical movement guide according to an embodiment of the present disclosure.

The vertical movement guide 200 may include one or more hole ports, and may include, for example, two hole ports as illustrated in FIG. 4.

The atrial sensor 300 may be connected to the atrial sensor re-coupling wire 600, and may include a first sensor 310.

The atrial sensor 300 may measure the electrical signals of the heart through the first sensor 310, and, for example, the atrial sensor 300 may measure ECG information, such as P waves, a QRS group, T waves or a Q-T time, an A-H time, and an H-V time.

Figure 2:
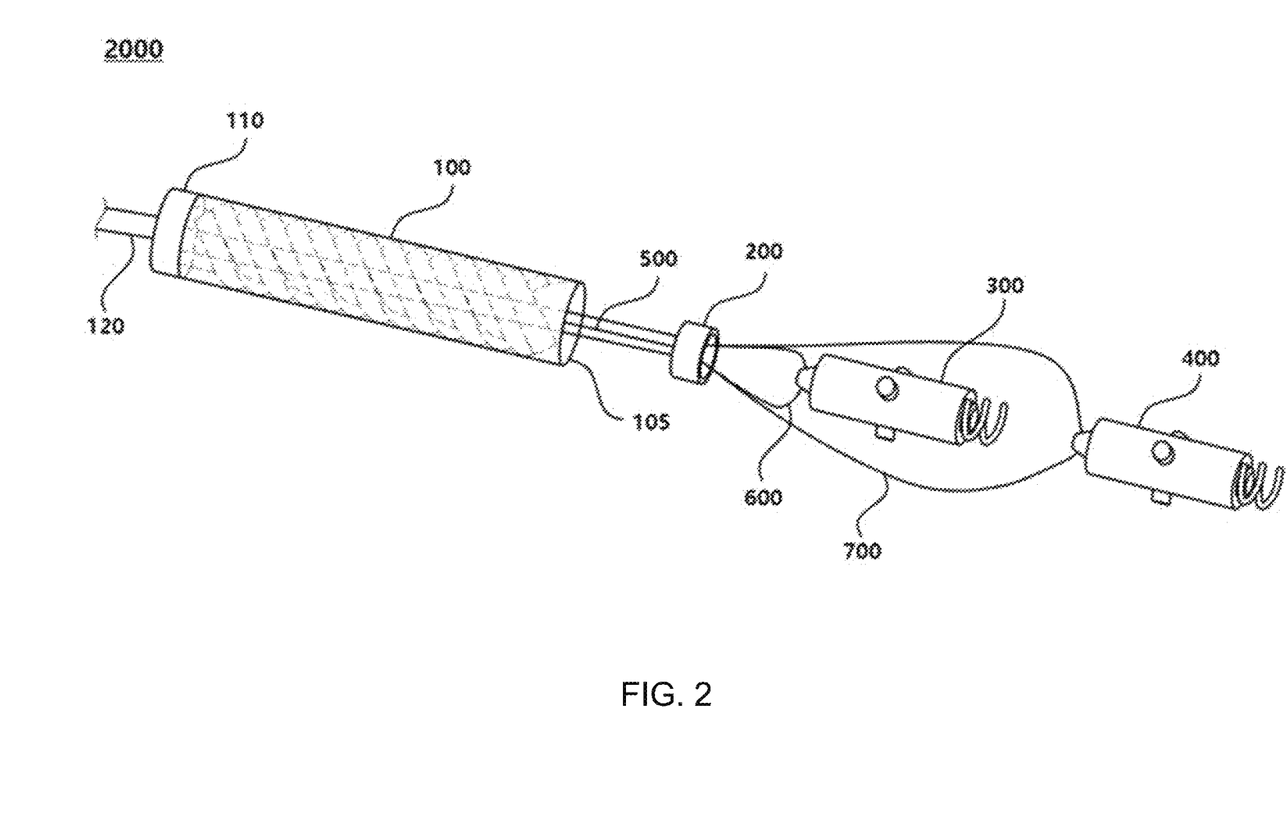
FIG. 2 is a view illustrating a pacemaker module according to another embodiment of the present disclosure.

The pacemaker 400 may be connected to the pacemaker re-coupling wire 700, and may include a stimulation unit (not illustrated) and a second sensor 410, through which cardiac stimulation pulses may be output and electrical signals in the ventricles may be measured. Accordingly, the pacemaker device 1000 or 2000 according to the present disclosure is capable of accurately measuring the electrical signals of the entire heart.

The stimulation unit may adjust stimulation strength and frequency of stimulation pulses based on the electrocardiogram information received from the atrial sensor 300, and may output cardiac stimulation pulses to the heart of a patient One or more atrial sensor re-coupling wires 600 may be included. For example, the pacemaker module 1000 may include two atrial sensor re-coupling wires.

The atrial sensor re-coupling wires 600 may be arranged to pass through the wire tube 120, the case unit 100, and the vertical movement guide 200, and to be connected to the atrial sensor 300.

Each of the atrial sensor re-coupling wires 600 may include a metal or synthetic fiber, and may include, for example, one or more materials selected from a group consisting of a shape memory alloy, carbon fiber, or nylon.

The atrial sensor re-coupling wires 600 may be used to move the atrial sensor 300 ejected to the outside of the case unit 100 or to move the atrial sensor 300 toward the wire tube 120 in the case unit 100. Specifically, it is possible for the user to move the atrial sensor 300 to the inside of the case unit 100 by moving the atrial sensor re-coupling wires 600 in a direction opposite to the ejection port 105 in the case unit 100, that is, toward the wire tube using the manipulation unit.

One or more pacemaker re-coupling wires 700 may be included. For example, the pacemaker module 1000 may include two pacemaker re-coupling wires.

The pacemaker re-coupling wires 700 may be arranged to pass through the wire tube 120, the case unit 100, and the vertical movement guide 200 and to be connected to the pacemaker 400.

Each of the pacemaker re-coupling wires 700 may include a metal or synthetic fiber, and may include, for example, one or more materials selected from a group consisting of a shape memory alloy, carbon fiber, or nylon.

Like the atrial sensor re-coupling wires 600 described above, the pacemaker re-coupling wires 700 may be used to move the atrial sensor 400 ejected to the outside of the case unit 100 or to move the atrial sensor 400 toward the wire tube 120 in the case unit 100.

The vertical movement guide 200, the atrial sensor 300, and the pacemaker 400 may be arranged in the order of the vertical movement guide 200, the atrial sensor 300, and the pacemaker 400 from the wire tube 120, as illustrated in FIG. 1.

Meanwhile, as illustrated in FIG. 1, the atrial sensor 300 and the pacemaker 400 may be connected to each other in a wired manner. Therefore, after both the atrial sensor 300 and the pacemaker 400 are placed in the heart of a patient, the atrial sensor 300 and the pacemaker 400 is capable of exchanging electrical signals through the data transmission wire 800. Specifically, the atrial sensor 300 is capable of transmitting measured ECG information to the pacemaker 400 through the data transmission wire 800, and the pacemaker 400 is capable of outputting cardiac stimulation pulses to the heart of a patient based on the information measured by the atrial sensor 300.

FIG. 2 is a view illustrating a pacemaker module according to another embodiment of the present disclosure.

Referring to FIG. 2, a pacemaker module 2000 according to another embodiment may include a case unit 100, a vertical movement guide 200, an atrial sensor 300, a pacemaker 400, a vertical movement guide wire 500, an atrial sensor re-coupling wire 600, and a pacemaker re-coupling wire 700.

As illustrated in FIG. 2, the atrial sensor 300 and the pacemaker 400 may be connected to each other in a wireless manner. Accordingly, after both the atrial sensor 300 and the pacemaker 400 are arranged in the heart of a patient, the ECG information measured by the atrial sensor 300 is capable of being transmitted to the pacemaker 400 in a wireless form, and the pacemaker 400 is capable of outputting cardiac stimulation pulses to the heart of the patient based on the information measured by the atrial sensor.

Figure 3:
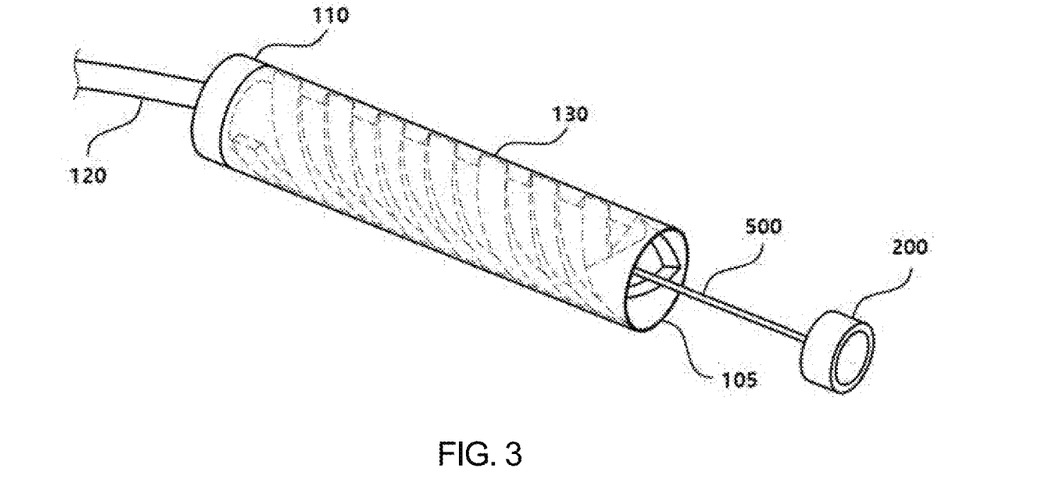
FIG. 3 is a view illustrating a case unit, a vertical movement guide, and a vertical movement guide wire according to an embodiment of the present disclosure.

FIG. 3 is a view illustrating a case unit 100, a vertical movement guide 200, and a vertical movement guide wire 500 according to an embodiment of the present disclosure.

Referring to FIG. 3, a rotational motion guide 130 may be arranged on the inner surface of the case unit 100. In addition, the rotational motion guide 130 may be arranged on the inner surface along the longitudinal direction of the case unit 100.

The rotational motion guide 130 may include a recess, and the recess may have a curved, straight, or spiral shape, and may be, for example, a spiral shape as illustrated in FIG. 3.

As will be described later, since the rotational motion guide 130 includes the spiral recess, the vertical movement guide 200 moves linearly by the user, and the atrial sensor 300 and the pacemaker 400 rotate while being pushed to the ejection port in the case unit by the vertical movement guide 200, which moves linearly, thereby providing a force to cause the fixing part to penetrate a heart portion.

Figure 5A:
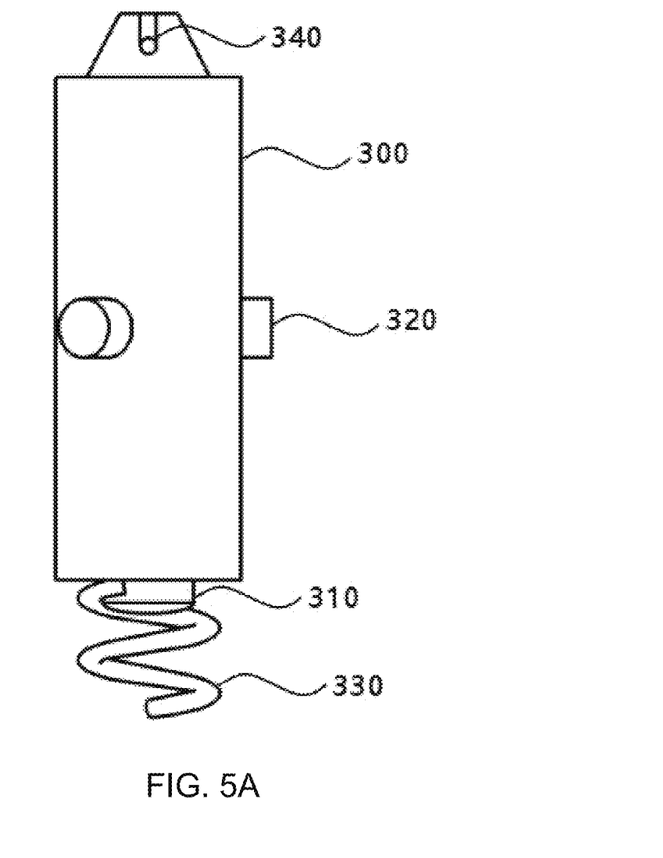
FIG. 5A is a view illustrating an atrial sensor according to an embodiment of the present disclosure.
Figure 5B:
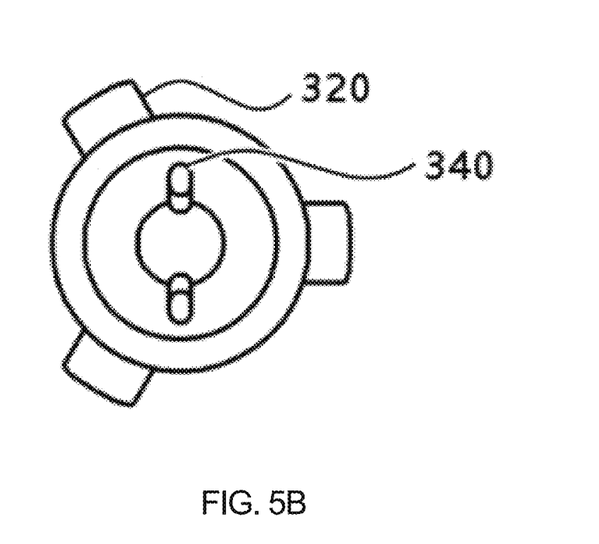
FIG. 5B is a front view of the atrial sensor according to an embodiment of the present disclosure.
Figure 5C:
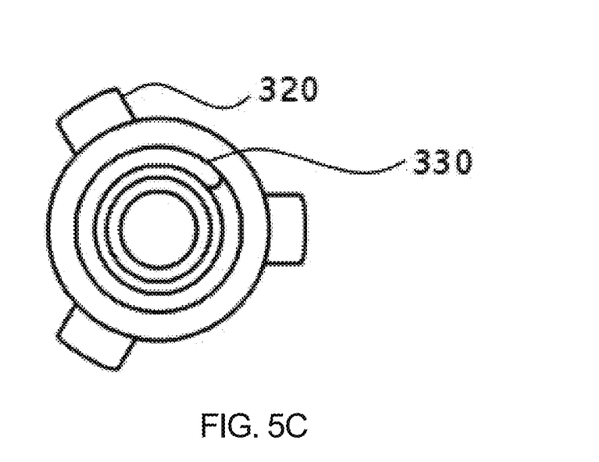
FIG. 5C is a rear view of the atrial sensor according to an embodiment of the present disclosure.

FIG. 5A is a view illustrating an atrial sensor according to an embodiment of the present disclosure, FIG. 5B is a front view of the atrial sensor according to an embodiment of the present disclosure, and FIG. 5C is a rear view of the atrial sensor according to an embodiment of the present disclosure.

Referring to FIGS. 5A to 5C, the atrial sensor 300 may include a first sensor 310, a first protrusion 320, a first fixing part 330, and a first re-coupling loop 340.

The first sensor 310 may be arranged at one end of the atrial sensor 300, and may measure the ECG information of a heart and an atrium.

The atrial sensor 300 may include one or more first protrusions 320. The first protrusion 320 may have a diameter corresponding to the width of the rotational motion guide 130. The first protrusion 320 may be arranged on the side surface of the atrial sensor 300. Accordingly, the first protrusion 320 is engageable with the recess in the rotational motion guide 130 of the case unit 100, and is capable of causing the atrial sensor 300 to rotate and move inside the case unit 100.

The first fixing unit 330 may be arranged at one end of the atrial sensor 300. The first fixing part 330 may be formed in a straight line, curved line, or spiral shape, and may be formed in a spiral shape as illustrated in FIG. 5A. In the case in which the first fixing part 330 is formed in a spiral shape, when the atrial sensor 300 rotates, the first fixing part 330 also rotates at the same time and penetrates into the heart tissue to stably fix the atrial sensor to the heart of a patient.

The atrial sensor 300 may include one or more first re-coupling loops 340, and the first re-coupling loops 340 may be arranged at the other end of the atrial sensor 300. The atrial sensor 300 may include two first re-coupling loops 340. In the case in which two or more first re-coupling loops are included, the one or more atrial sensor re-coupling wires are fixed to the first re-coupling loops, respectively, so that the atrial sensor can be moved in a more balanced manner when the atrial sensor is moved.

The atrial sensor 300 may include a first battery unit (not illustrated), and the first battery unit may supply power for driving the atrial sensor. The first battery unit may include a lithium ion battery, a fuel cell, or a biofuel cell.

The atrial sensor 300 may include a transmission unit (not illustrated), and the transmission unit may transmit the electrocardiogram information of a heart measured by the atrial sensor to the pacemaker.

Figure 6A:
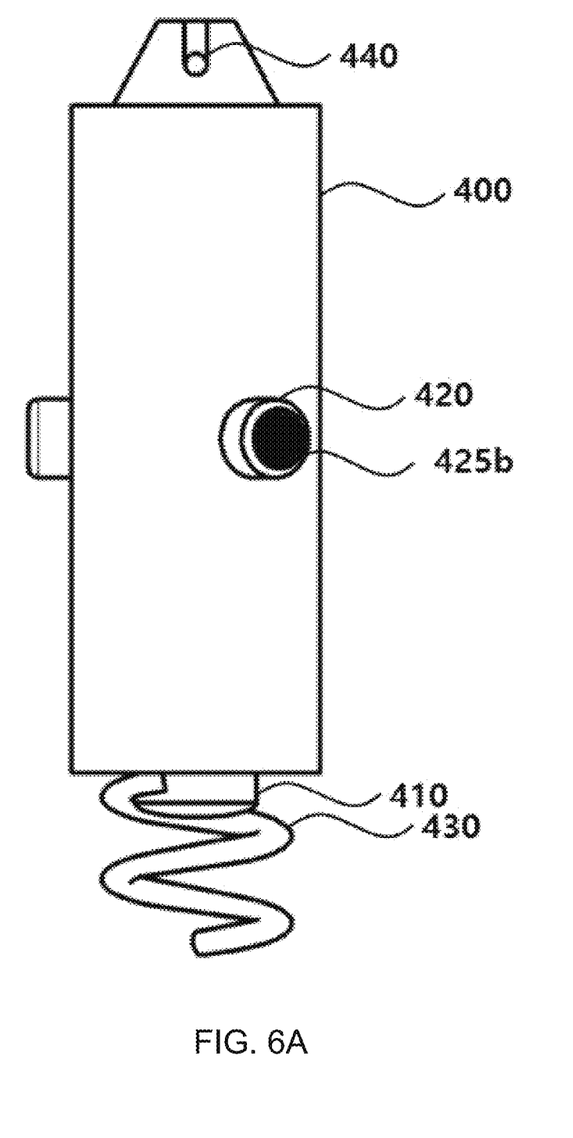
FIG. 6A is a view illustrating a pacemaker according to an embodiment of the present disclosure.
Figure 6B:
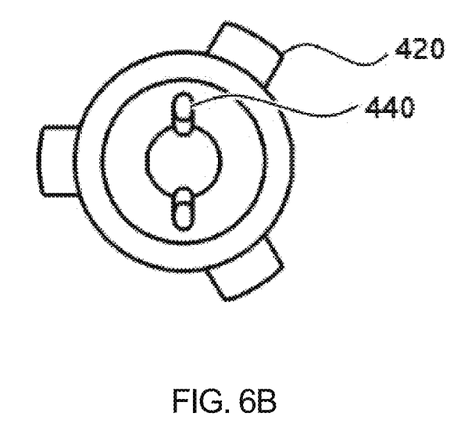
FIG. 6B is a front view of the pacemaker according to an embodiment of the present disclosure.
Figure 6C:
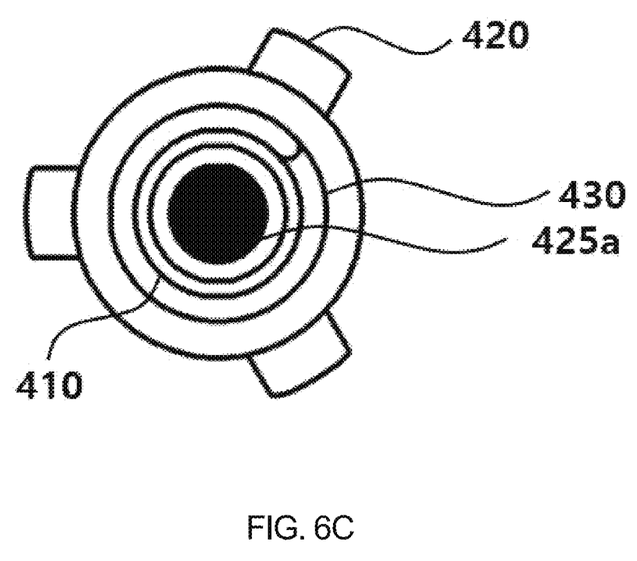
FIG. 6C is a rear view of the pacemaker according to an embodiment of the present disclosure.

FIG. 6A is a view illustrating a pacemaker according to an embodiment of the present disclosure, FIG. 6B is a front view of the pacemaker according to an embodiment of the present disclosure, and FIG. 6C is a rear view of the pacemaker according to an embodiment of the present disclosure.

Referring to FIGS. 6A to 6C, a pacemaker 400 may include a second sensor 410, a magnetic pole unit (not illustrated), a second protrusion 420, a second fixing part 430, and a second re-coupling loop 440.

The stimulation unit (not illustrated) may be arranged inside or outside the pacemaker 400, and the stimulation unit may output cardiac stimulation pulses.

The stimulation unit (not illustrated) may include electrodes 425a and 425b.

The second sensor 410 may be arranged at one end of the pacemaker 400, and may measure electrical signals from a ventricle. The electrode 425a may be arranged on a surface of the second sensor 410, and the stimulation unit may output cardiac stimulation pulses through the electrode 425b arranged on the surface of the second sensor 410.

The pacemaker 400 may include at least one second protrusion 420, and the second protrusion 420 may have a diameter corresponding to the width of the rotational motion guide 130. The second protrusion 420 may be arranged on the side surface of the pacemaker 400. Accordingly, the second protrusion 420 may be engageable with the recesses 130 in the rotational motion guide 130 in the case unit 100 so as to cause the pacemaker 400 to rotate and move inside of the case unit.

The electrode 425b may be arranged on the surface of the second protrusion 420. Accordingly, the stimulation unit may output cardiac stimulation pulses through the electrode of the second protrusion 420, and accordingly, the cardiac stimulation pulses may also be output from a side surface portion of the pacemaker 400.

The second fixing part 430 may be arranged at one end of the pacemaker 400. The second fixing part 430 may be formed in a straight line, curved line or spiral shape, and may be formed in a spiral shape as illustrated in FIG. 6A. In the case in which the second fixing part 430 is formed in a spiral shape, when the pacemaker 400 rotates, the second fixing part 430 also rotates at the same time and penetrates into the heart tissue to stably fix the pacemaker to the heart of a patient.

The pacemaker 400 may include at least one second re-coupling loop 440, and the second re-coupling loop 440 may be arranged at the other end of the pacemaker 400. The pacemaker 400 may include two second re-coupling loops 440. When two or more second re-coupling loops 440 are included, at least one pacemaker re-coupling wire 700 is fixed to each of the second re-coupling loop, thereby enabling the pacemaker to move in a more balanced manner.

The pacemaker 400 may include a second battery unit (not illustrated), and the second battery unit may supply power for driving the pacemaker. The second battery unit may include a lithium ion battery, a fuel cell, or a biofuel cell.

The pacemaker 400 may include a reception unit (not illustrated) configured to receive an electrical signal from the atrial sensor 300.

Figure 7:
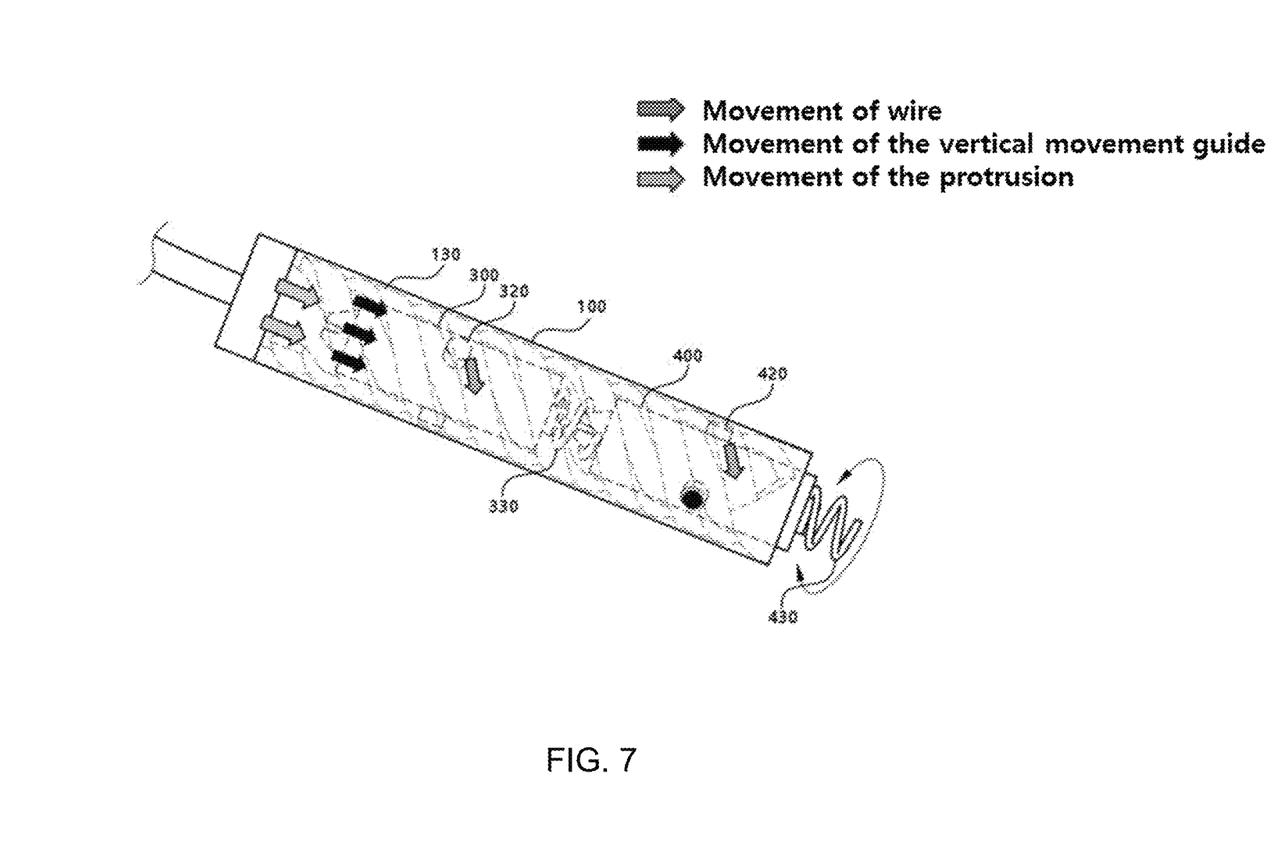
FIG. 7 is a view illustrating movements of a vertical movement guide, a vertical movement guide wire, and a protrusion when an atrial sensor and a pacemaker are fixed in a pacemaker module according to an embodiment of the present disclosure.
Figure 8:
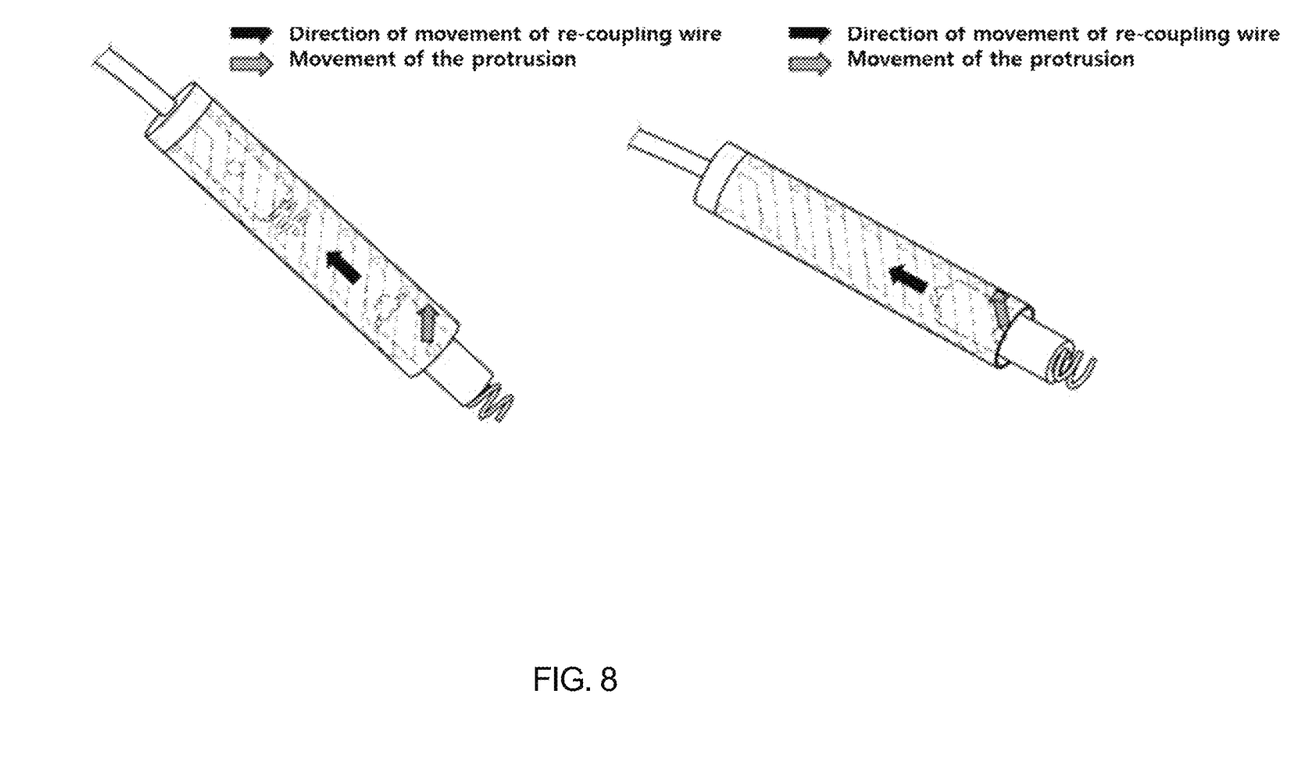
FIG. 8 is a view illustrating movements of a vertical movement guide, a vertical movement guide wire, and a protrusion during re-coupling of an atrial sensor or a pacemaker in a pacemaker module according to an embodiment of the present disclosure.

FIG. 7 is a view illustrating movements of a vertical movement guide, a vertical movement guide wire, and a protrusion when an atrial sensor and a pacemaker are fixed in a pacemaker module according to an embodiment of the present disclosure, and FIG. 8 is a view illustrating movements of a vertical movement guide, a vertical movement guide wire, and a protrusion during re-coupling of an atrial sensor or a pacemaker in a pacemaker module according to an embodiment of the present disclosure.

Referring to FIGS. 7 to 8, it is possible for the user to rotate and eject the atrial sensor 300 and the pacemaker 400 to the outside of the case unit by operating the vertical movement guide wire 500.

Specifically, referring to FIG. 7, when the user moves the vertical movement guide wire 500 toward the ejection port 105 in the case unit, the vertical movement guide 200 pushes the atrial sensor 300 and the pacemaker 400 toward the ejection port 105. In this case, since the side surfaces of the atrial sensor 300 and the pacemaker 400 include protrusions 320 and 420, which are engaged with recess in the rotational motion guide 130, the protrusions spirally move along the recess. In addition, as each of the protrusions arranged on the atrial sensor 300 and the pacemaker 400 spirally moves toward the ejection port 105, the atrial sensor 300 and the pacemaker 400 are movable to the outside of the case unit 100 while moving. When the atrial sensor 300 and the pacemaker 400 rotate, the first fixing part 330 and the second fixing part 430 rotate, and the first fixing part 330 and the second fixing part 430 penetrate into the heart tissue of a patient while rotating. Thus, it is possible to firmly fix the atrial sensor 300 and the pacemaker 400 in the heart.

In addition, as illustrated in FIG. 8, by moving the atrial sensor re-coupling wire 600 and the pacemaker re-coupling wire 700 toward the wire tube 120, it is possible for the user to move the atrial sensor 300 and the pacemaker 400 into the case unit 100. When the atrial sensor 300 or the pacemaker 400 is directed to the inside of the case unit, the atrial sensor 300 or the pacemaker 400 is introduced into the inside of the case unit while being rotated by the protrusions arranged on the side surface thereof and the rotational motion guide 130, as described above. In addition, when the atrial sensor and pacemaker are placed inside the case unit, the atrial sensor 300 and the pacemaker 400 are stably fixed inside the case unit by the protrusions. Thus, it is possible to prevent the atrial sensor 300 and the pacemaker 400 from moving regardless of the user's intension.

Figure 9:
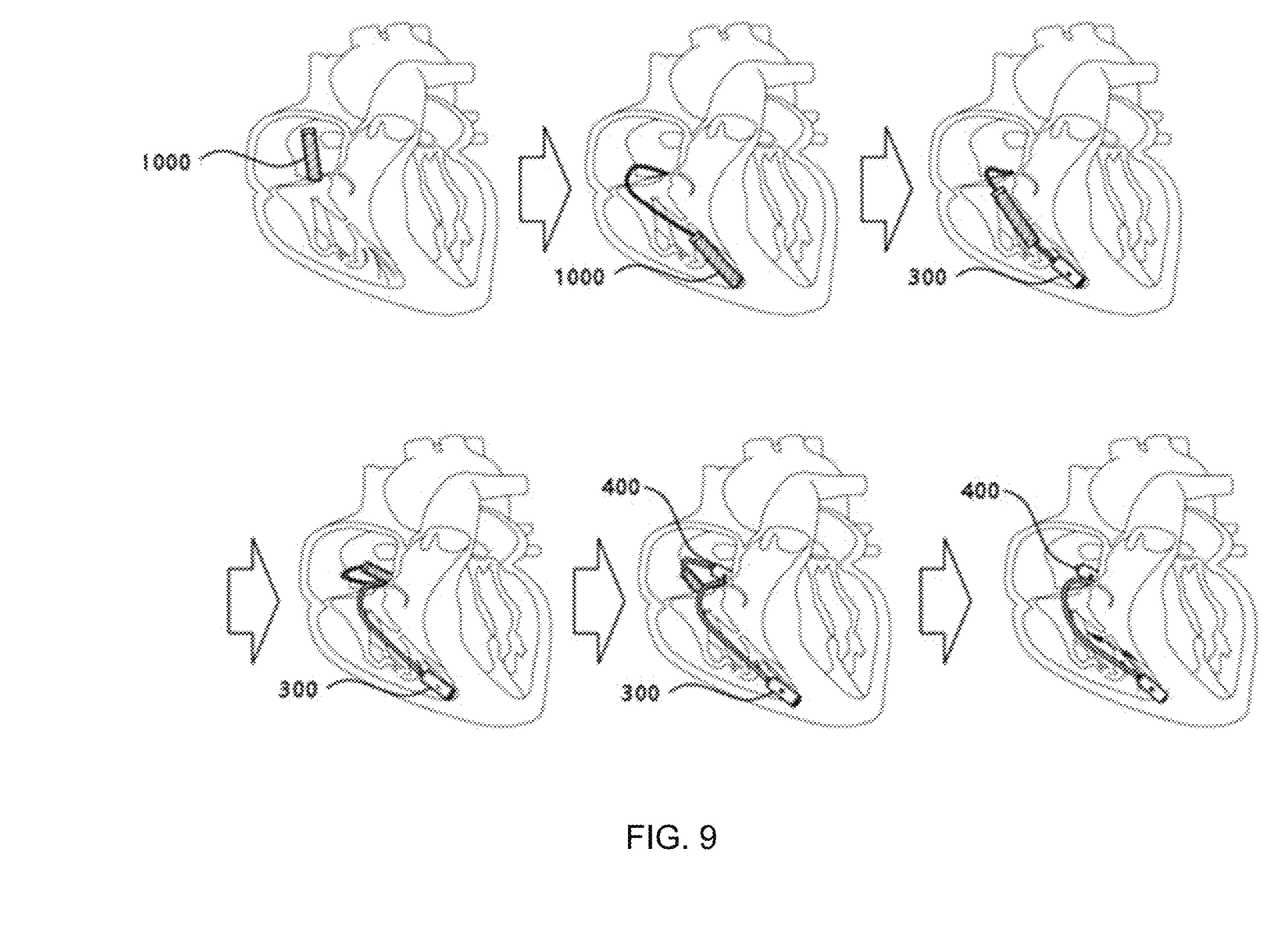
FIG. 9 is a view illustrating a process of implanting a pacemaker module according to an embodiment of the present disclosure into a heart.
Figure 10:
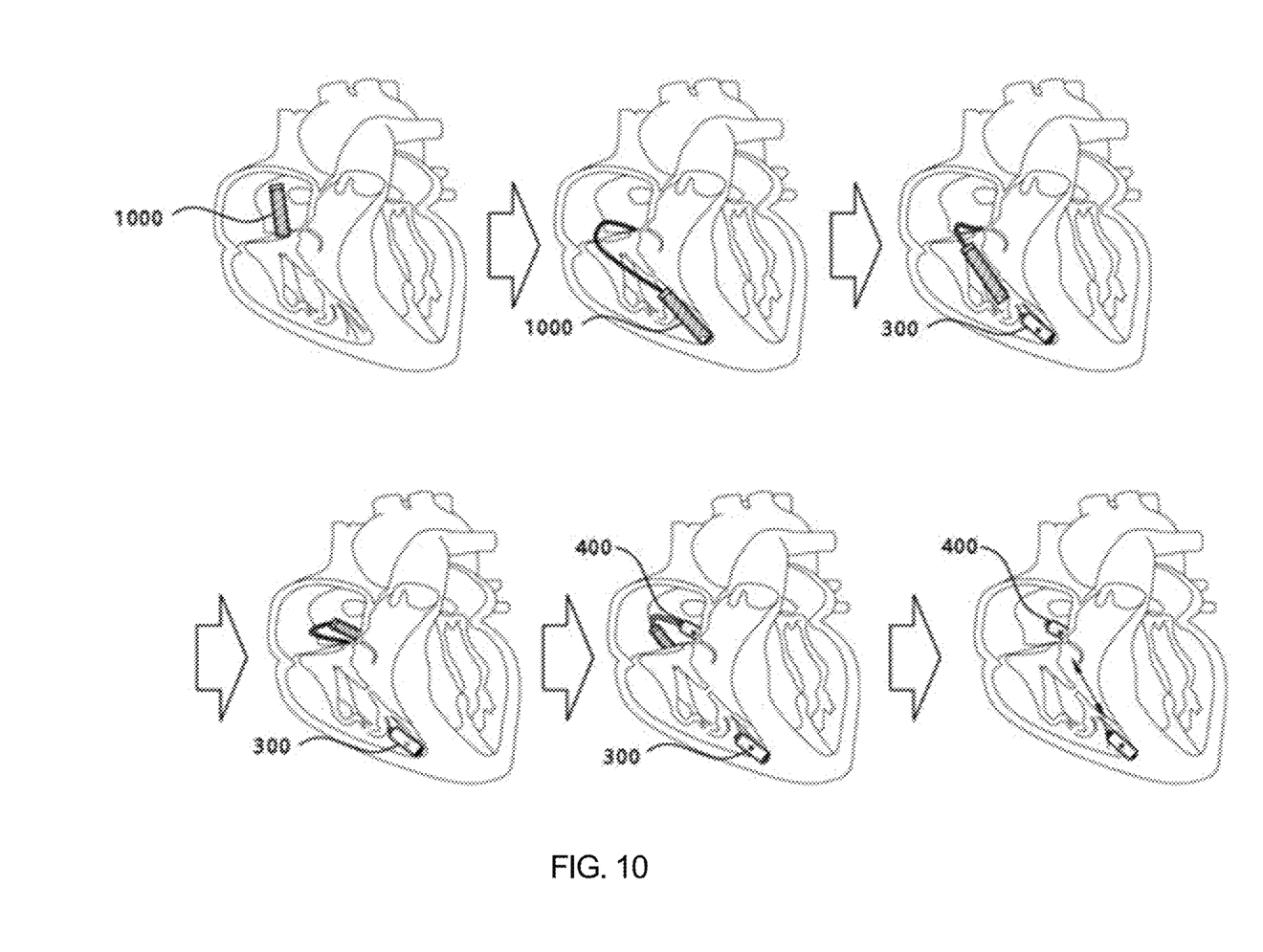
FIG. 10 is a view illustrating a process of implanting a pacemaker module according to another embodiment of the present disclosure into a heart.

FIG. 9 is a view illustrating a process of implanting a pacemaker module according to an embodiment of the present disclosure into a heart, and FIG. 10 is a view illustrating a process of implanting a pacemaker module according to another embodiment of the present disclosure into a heart.

As illustrated in FIGS. 9 to 10, the user may place the atrial sensor and the pacemaker of a pacemaker module in the heart of a patient.

Specifically, first, the user moves the pacemaker module to the right ventricle through the right atrium through the inferior vena cava, implants and fixes the pacemaker 400 on the inner wall of the right ventricle by manipulating the vertical movement guide, and checks the operation of the pacemaker module. At this time, as described above, the pacemaker is ejected to the outside of the case while rotating, and accordingly, the second fixing part 430 is firmly fixed to the heart tissue. Thereafter, the user moves the pacemaker module back to the right atrium, implants and fixes the atrial sensor 300 by manipulating the vertical movement guide 200 once again, and checks the operation of the pacemaker module. After the atrial sensor 300 and the pacemaker 400 are implanted in the heart of the patient, the user draws out the case unit 100, the atrial sensor re-coupling wire 500, and the pacemaker re-coupling wire 600 through the inferior vena cava, thereby finishing the implantation process. The implanted atrial sensor 300 and pacemaker 400 is capable of measuring ECG information of a patient and capable of applying appropriate cardiac stimulation pulses while transmitting and receiving data in a wired or wireless manner.

Meanwhile, during the implantation process, it is possible for the user to precisely and consistently move the pacemaker modules 1000 and 2000 to a desired location through the magnetic body 100 included in the case unit 100. In addition, it is possible for a user to firmly fix the atrial sensor 300 and the pacemaker 400 to the inner wall of the heart only by pushing the vertical movement guide 200. Thus, the pacemaker module can be accurately implanted into the heart of a patient without being greatly restricted by the skill of a practitioner.

DESCRIPTION OF REFERENCE NUMERALS

100: case unit, 200: vertical movement guide, 300: atrial sensor, 400: pacemaker, 500: vertical movement guide wire, 600: atrial sensor re-coupling wire, 700: pacemaker re-coupling wire, 800: data transmission wire, 105: ejection port, 130: rotational motion guide, 310: first sensor, 320: first protrusion, 330: first fixing part, 340: first re-coupling loop, 410: second sensor, 420: second protrusion, 430: second fixing part, 440: second re-coupling loop

INDUSTRIAL APPLICABILITY

The present disclosure relates to a multi leadless pacemaker and surgical device. More specifically, the present disclosure relates to a pacemaker module in which a case unit, a vertical movement guide, an atrial sensor, and a pacemaker are integrated. The pacemaker module according to the present disclosure is capable of preventing damage to the inside of a human body during implantation, and capable of controlling the heartbeat while measuring the microcurrent and current flow of the heart.

What is claimed is:

1. A pacemaker module comprising:
a case unit through which a vertical movement guide wire, an atrial sensor re-coupling wire, and a pacemaker re-coupling wire pass;
a vertical movement guide connected to the vertical movement guide wire and including a hole port through which the atrial sensor re-coupling wire and the pacemaker re-coupling wire pass;
an atrial sensor connected to the atrial sensor re-coupling wire and including a first sensor and a first fixing part; and
a pacemaker connected to the pacemaker re-coupling wire and including a second sensor and outputting cardiac stimulation pulses and a second fixing part,
wherein the case unit includes a magnetic body,
wherein the pacemaker module is moved by applying a magnetic field to the magnetic body of the case unit,
wherein the vertical movement guide wire, the atrial sensor re-coupling wire, and the pacemaker re-coupling wire are independently movable according to a user's manipulation,
wherein the vertical movement guide, the atrial sensor, and the pacemaker are arranged in the order of the vertical movement guide, the atrial sensor, and the pacemaker from the side opposite to an ejection port in the case unit, wherein the case unit includes a rotational motion guide arranged on an inner surface thereof, the rotational motion guide includes a recess, and the recess has a spiral shape,
wherein the first fixing part and the second fixing part each have a spiral shape,
wherein the atrial sensor and the pacemaker are moved into the case unit by moving the atrial sensor re-coupling wire and the pacemaker re-coupling wire into the case unit, and
wherein the atrial sensor and the pacemaker rotate while being pushed to the ejection port in the case unit by the vertical movement guide, which moves linearly, thereby providing a force to cause the first fixing part and the second fixing part to penetrate a heart portion.

2. The pacemaker module of claim 1, wherein the atrial sensor and the pacemaker are connected to each other via a data transmission wire.

3. The pacemaker module of claim 1, wherein the magnetic body is a permanent magnet.

4. The pacemaker module of claim 1, wherein the atrial sensor includes at least one first protrusion configured to be engageable with the rotational motion guide, and
the pacemaker includes at least one second protrusion configured to be engageable with the rotational motion guide.

5. The pacemaker module of claim 1, wherein the atrial sensor further includes a first re-coupling loop, and the atrial sensor re-coupling wire is connected to the atrial sensor via the first re-coupling loop.

6. The pacemaker module of claim 5, wherein the pacemaker further includes a second re-coupling loop, and the pacemaker re-coupling wire is connected to the pacemaker via the second re-coupling loop.

7. The pacemaker module of claim 1, wherein the second sensor includes an electrode arranged on a surface of the second sensor thereof.

* * * * *